United States Patent
Mazoyer et al.

(10) Patent No.: US 9,643,945 B2
(45) Date of Patent: May 9, 2017

(54) PROCESS FOR THE PREPARATION OF 2,5-FURAN-DICARBOXYLIC ACID

(71) Applicant: Furanix Technologies B.V., Amsterdam (NL)

(72) Inventors: Etienne Mazoyer, Amsterdam (NL); Ana Sofia Vagueiro De Sousa Dias, Amsterdam (NL); Benjamin McKay, Amsterdam (NL); Hendrikus Jacob Baars, Amsterdam (NL); Victor Peter Charles Vreeken, Amsterdam (NL); Gerardus Johannes Maria Gruter, Amsterdam (NL); David Lee Sikkenga, Wheaton, IL (US)

(73) Assignee: FURANIX TECHNOLOGIES B.V., Amsterdam (NL)

( * ) Notice: Subject to any disclaimer, the term of this patent is extended or adjusted under 35 U.S.C. 154(b) by 0 days.

(21) Appl. No.: 14/781,993

(22) PCT Filed: Apr. 4, 2014

(86) PCT No.: PCT/NL2014/050211
§ 371 (c)(1),
(2) Date: Oct. 2, 2015

(87) PCT Pub. No.: WO2014/163500
PCT Pub. Date: Oct. 9, 2014

(65) Prior Publication Data
US 2016/0024039 A1    Jan. 28, 2016

(30) Foreign Application Priority Data

Apr. 5, 2013 (NL) .................................. 2010572

(51) Int. Cl.
*C07D 307/68*    (2006.01)

(52) U.S. Cl.
CPC .......... *C07D 307/68* (2013.01); *Y02P 20/582* (2015.11)

(58) Field of Classification Search
CPC .......................... C07D 307/68; Y02P 20/582
See application file for complete search history.

(56) References Cited

U.S. PATENT DOCUMENTS 8,242,292 B2    8/2012    Yutaka et al.

FOREIGN PATENT DOCUMENTS

| WO | 2010/132740 A2 | 11/2010 |
| WO | 2011/043660 A2 | 4/2011 |
| WO | 2012/161967 A1 | 11/2012 |

*Primary Examiner* — Samantha Shterengarts
*Assistant Examiner* — Matt Mauro

(57) ABSTRACT

2,5-Furandicarboxylic acid and methyl acetate are prepared in a continuous process by introducing a 5-methoxymethylfurfural-containing feedstock, an oxygen-containing gas, an oxidation catalyst and an acetic acid-containing solvent into a reactor; allowing 5-methoxymethylfurfural to react with oxygen and acetic acid in the presence of the oxidation catalyst to yield 2,5-furandicarboxylic acid as main product and methyl acetate; withdrawing 2,5-furandicarboxylic acid-containing product from the reactor and recovering 2,5-furandicarboxylic acid product; and withdrawing a vaporous stream containing methyl acetate from the reactor.

34 Claims, 1 Drawing Sheet

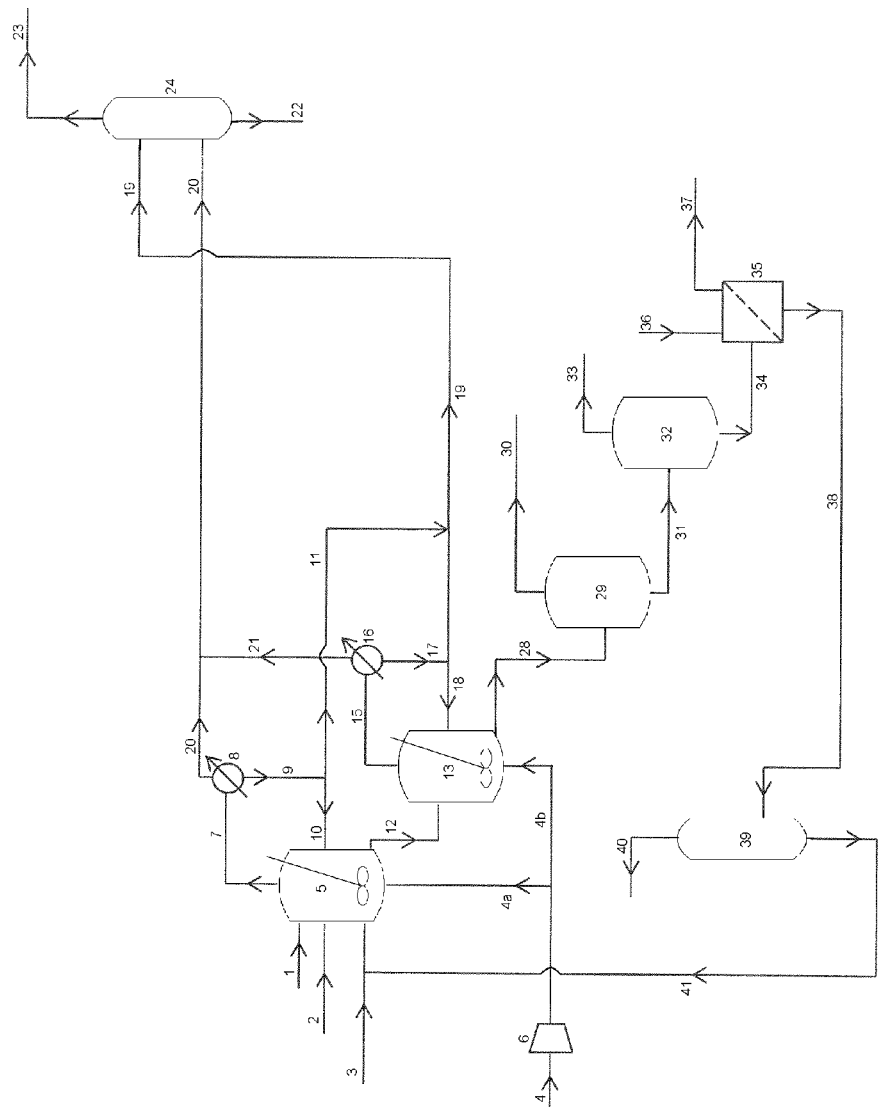

PROCESS FOR THE PREPARATION OF 2,5-FURAN-DICARBOXYLIC ACID

CROSS-REFERENCE TO RELATED APPLICATIONS

This application is the National Stage of International Application No. PCT/NL2014/050211 filed Apr. 4, 2014, which claims the benefit of Netherlands Application No. NL 2010572, filed Apr. 5, 2013, the contents of which is incorporated by reference herein.

FIELD OF THE INVENTION

The present invention relates to a process for the preparation of 2,5-furan-dicarboxylic acid, more in particular to a process for the preparation of 2,5-furan-dicarboxylic acid by the oxidation of methoxymethyl furfural. The oxidation is conducted in the presence of an oxidation catalyst and by means of an oxidizing gas. The oxidation takes place in a solvent.

BACKGROUND OF THE INVENTION

Recently there has been a growing interest in 2,5-furan-dicarboxylic acid ("FDCA") as an alternative monomer for the preparation of polyesters, polyamides, plasticizers and the likes. FDCA is obtainable from hydroxymethyl furfural, which can be produced from carbohydrates. In this way FDCA forms a biobased renewable alternative to other diacids, such a terephthalic acid, for the preparation of condensation polymers, such as polyethylene terephthalate.

The oxidation of hydroxymethyl furfural ("HMF") is known from WO 2010/132740. This document discloses the batch-wise oxidation of HMF in the presence of an oxidation catalyst comprising cobalt, manganese and bromide. Products of such oxidation include FDCA. The document further teaches that when an alkoxymethyl furfural is used as feedstock, the product is predominantly the mono-ester of FDCA. This is exemplified by the oxidation of butoxymethyl furfural, which yields 5-(butoxycarbonyl)furan-2-carboxylic acid as the main product.

In WO 2011/043660 a batch process is described wherein a 5-alkoxymethylfurfural or a 2,5-(dialkoxymethyl)furan is oxidized with an oxidizing gas in the presence of an oxidation catalyst. The catalyst comprises cobalt, manganese and bromide. In the examples methoxymethyl furfural and ethoxymethyl furfural are used as feedstock. The reaction product in the examples is a mixture of FDCA and the mono-ester of FDCA, wherein FDCA is the predominant product.

WO 2012/161967 discloses an oxidation process of a starting material that may be HMF, an ether of HMF or an ester of HMF with an oxidizing gas and a catalyst system comprising cobalt, manganese and bromine at a temperature of 100 to 220° C. The process may be conducted in a continuous mode, e.g. in a bubble column. The experiments in this document confirm the results of the reaction in WO 2011/043660, in that the oxidation of ethoxymethyl furfural in a semi-batch process yields a mixture of FDCA and the mono-ethyl ester of FDCA, wherein the predominant product is FDCA. The mono-ethyl ester of FDCA is considered an undesired by-product. Another contaminant that was found is 5-formyl-furan-2-carboxylic acid. The document further discloses in an embodiment that the product of the oxidation may be separated into a low impurity slurry stream which is subjected to a secondary oxidation. It is observed that care should be taken about the amount of oxygen fed to the secondary oxidation since there exists a risk of burning the organic molecules to $CO_2$.

The three prior art documents, i.e., WO 2010/132740, WO 2011/043660 and WO 2012/161967, all disclose that the oxidation reactions take place in a solvent. The most commonly used solvent is acetic acid or glacial acetic acid.

The experiments have been conducted in batch mode or semi-batch mode. None of the prior art documents refer to volatile impurities. It is believed that any volatile organic compound has been oxidized to $CO_2$, as indicated in WO 2012/161967. Therefore, no problem seems to occur regarding volatile by-products.

SUMMARY OF THE INVENTION

The present inventors have now found that when the oxidation of methoxymethylfurfural is conducted in a continuous process and in the presence of an acetic acid-containing solvent and an oxidation catalyst, there is a tendency for methyl acetate to be formed. This problem has not been recognized in the prior art, but it may become an important issue in commercial continuous processes. It has now surprisingly been found that the yield of FDCA from methoxymethyl furfural can be optimized and the occurrence of impurities can be minimized if in a continuous process a methyl acetate-containing vaporous stream is withdrawn from the reactor wherein the reaction takes place.

Accordingly, the present invention provides a continuous process for the preparation of 2,5-furandicarboxylic acid and methyl acetate, comprising introducing a 5-methoxymethylfurfural-containing feedstock, an oxygen-containing gas, an oxidation catalyst and an acetic acid-containing solvent into a reactor;

allowing 5-methoxymethylfurfural to react with oxygen and acetic acid in the presence of the oxidation catalyst to yield 2,5-furandicarboxylic acid as main product and methyl acetate;

withdrawing 2,5-furandicarboxylic acid-containing product from the reactor and recovering 2,5-furandicarboxylic acid product; and withdrawing a vaporous stream containing methyl acetate from the reactor.

By the withdrawal of the vaporous stream not only methyl acetate is withdrawn from the reaction mixture, but also methanol that is liberated in the oxidation reaction is withdrawn at the same time. This has the advantage that the valuable by-product of methyl acetate is not wasted or combusted by any further oxidation but is available for subsequent recovery. Surprisingly it has been found that the withdrawal of the vaporous stream will also lead to the reduced combustion of methanol and the reduced formation of methyl bromide. The withdrawn vaporous stream containing methyl acetate may also comprise some of the water that is formed in the esterification reaction of methanol with acetic acid.

In this context reference is made to U.S. Pat. No. 8,242,292 that discloses the oxidation of HMF to FDCA. In the reaction water is formed and water vapor and acetic acid are removed from the reaction. The water is subsequently caught by a dehydration agent to absorb water and acetic acid is recycled to the reaction. It is evident that in this process no methyl acetate is formed. In addition, in the oxidation of HMF to FDCA no volatile organic products are formed that may be combusted to $CO_2$. Also in this patent document the experiments have been conducted in a batch mode. Therefore, the skilled person would not get any suggestion from U.S. Pat. No. 8,242,292 that a problem could arise in a continuous process using methoxymethyl furfural ("MMF") as starting material.

The skilled person will understand that the continuous process does not require that necessarily the withdrawal of the vaporous stream and/or the FDCA-containing product is also done continuously. Although it is preferred to perform the withdrawal of both the vaporous stream and the FDCA-containing product continuously, it is also possible to withdraw the vaporous stream and FDCA-containing product intermittently. The continuous process according to the present invention merely requires that the starting materials, i.e. the feedstock, the acetic acid-containing solvent and the oxygen-containing gas are introduced continuously into the reactor. Even the catalyst may be added intermittently.

It is evident that the starting materials may be added as separate streams. However, it is also feasible to combine one or more of the starting materials in a combined stream. Such is especially advantageous for the feedstock and the acetic-acid-containing solvent. The thus combined stream may further comprise the catalyst. The oxygen-containing gas is typically introduced as a separate stream.

The feedstock contains 5-methoxymethyl furfural. The feedstock may also contain other furan components. A suitable furan compound that may be contained in the feedstock is 5-hydroxymethyl furfural. The amount of 5-hydroxymethyl furfural may be up to 20% wt, based on the feedstock. Suitably, the feedstock consists for 50 to 100% wt, in particular from 90 to 100% wt of 5-methoxymethyl furfural.

The feedstock is typically dissolved in the acetic acid-containing solvent. In this way the transportation of both the solvent and the feedstock becomes easy. The acetic acid-containing solvent may range from glacial acetic acid to aqueous solutions of acetic acid. Preferably, the acetic acid-containing solvent is glacial acetic acid, since this facilitates the esterification reaction of liberated methanol to methyl acetate without water formation. Since methyl acetate is more difficult to oxidize to $CO_2$ than methanol, the formation of methyl acetate minimizes the oxidation of methanol to $CO_2$. In this way valuable methyl acetate can be recovered. In practice, the acetic acid-containing solvent comprises some water, e.g. from 1 to 15% wt, preferably from 2 to 6% wt water, based on the weight of the solvent. Since a part of the methanol is withdrawn in the vaporous stream together with methyl acetate, this part is not available for the esterification to methyl acetate with concurrent water formation. Moreover, since it has been withdrawn it cannot be oxidized to $CO_2$ and water. In this way, the amount of water in the reaction mixture is tolerable so that not all water that is formed or is present in the reaction mixture needs to be removed. At the same time the relative amounts of water and acetic acid will be relatively low, so that the amount of solvent in the reactor may be easily kept more or less constant. Methanol that is being withdrawn may be recovered and be used in the process, e.g. in the manufacture of 5-(methoxymethyl)furfural from carbohydrates.

The relative amount of 5-(hydroxymethyl)furfural that is being introduced into the reactor suitably ranges from 2 to 50% wt, based on the combined weight of the feedstock, catalyst and solvent. Higher relative amounts of 5-(methoxymethyl)furfural may lead to products in such high solids concentration that it may cause transportation problems in subsequent steps. At concentrations below 2% wt, the process becomes commercially unattractive.

It has been found that the oxidation takes place readily when an oxidizing gas, comprising free oxygen is being used. The concentration of oxygen in the oxidizing gas may vary between wide ranges. It is therefore feasible to use substantially pure oxygen. The potential drawback of using such a concentrated oxygen stream resides in the risk of the formation of explosive mixtures. It is therefore advantageous to use gas comprising less oxygen. At very low oxygen concentrations in the oxidizing gas, e.g., at 1 to 3% vol, based on the volume of the oxygen-containing gas, a negative effect on the oxidation is achieved. The oxygen level may be below the oxygen concentration in air. The oxidizing gas preferably comprises from 6 to 22% vol of oxygen, based on the volume of the oxygen-containing gas. This may be prepared by depleting air from oxygen or by partial air separation and using air or an oxygen-lean air stream. In this way the oxygen-containing gas comprises sufficient oxygen to ensure a smooth oxidation, whereas it is relatively easy to ascertain that the oxygen concentration in the vaporous stream is kept below a level, e.g. at a level of at most 10 or 8% vol, based on the volume of the vaporous stream, where explosive mixtures can be formed. It is most preferred to use air. It is understood that the concentration of the oxygen is taken at the introduction of the oxygen-containing gas into the reactor. It is evident that the oxygen concentration is reduced during the oxidation reaction. That preferably results in an outlet concentration of oxygen in the range of 1 to 10 vol %, preferably 1 to 5 vol %, based on the volume of the vaporous stream that is being withdrawn from the reactor.

The catalyst is preferably a similar catalyst to those that have been used in the reactions according to WO 2010/132740, WO 2011/043660 and WO 2012/161967. That means that the oxidation catalyst preferably comprises at least one metal selected from the group consisting of cobalt and manganese, more preferably comprises both cobalt and manganese. The oxidation catalyst that comprises both cobalt and manganese preferably contains cobalt and manganese in an atomic ratio ranging from 1:1 to 100:1. It has appeared that it is advantageous that the atomic amount of cobalt exceeds that of manganese. The metals are suitably added as a salt that dissolves in the acetic-acid containing solvent. Suitable salts are the acetate salts, since in this way no unnecessary other anions are being introduced into the reactor. Moreover, as the present process is a continuous process the cobalt and/or manganese components may become available in the form of the acetate salts, e.g. via a recycle of acetic acid solvent. In such a case the catalyst components are also suitably added in the form of their acetate salts. However, also the halide salts are feasible, especially the bromide salts. Alternatively, the anion may suitably be the furan-dicarboxylate ion. Also in this way, no extraneous ions are introduced into the reaction mixture.

Such is particularly the case when the catalyst comprises a source of bromide. As disclosed in the prior art documents WO 2010/132740, WO 2011/043660 and WO 2012/161967 the oxidation catalysts preferably contain a source of bromide. The source can be a salt, such as the bromide salt of an alkali metal or alkaline earth metal, in particular sodium bromide, but also hydrobromic acid can be used. The use of the latter has preference, since during the conducting of the reaction there may be losses of bromide, e.g. in the form of methyl bromide, as indicated in WO 2012/161967. In such cases there may be a build-up of residual sodium ions. That is avoided when hydrobromic acid is used. Bromide may also be introduced via recycle of acetic acid. The amount of the source of bromide is preferably selected such that the atomic ratio of cobalt and manganese exceeds that of bromide. That would mean that the atomic ratio of (Co+Mn)>Br.

Although excellent oxidation results are obtainable with the use of a catalyst that comprises cobalt, manganese and optionally bromide, the catalyst may comprise one or more further catalytically active metals. Such metals include metals selected from the group consisting of zirconium, cerium, nickel, molybdenum, hafnium, zinc, chromium, ruthenium, iron and mixtures thereof.

The catalyst amounts may be selected within wide ranges. Typically, the amount of cobalt is selected in the range of 500 to 6000 ppm by weight, based on the weight of the feedstock, solvent and oxidation catalyst. The amount of manganese, if used, may optionally be selected as a similar or smaller amount, typically in the range from 20 to 6000 ppm by weight, based on the weight of the feedstock, solvent and oxidation catalyst. As indicated above, the amount of bromide in moles is preferably at most equal to the amount of cobalt and manganese together. Typically, the bromide concentration would be from 30 to 8000, preferably 50 to 4500 ppm by weight of bromide, based on weight of the feedstock, solvent and catalyst.

The oxidation process according to the present invention can be carried out in one reactor. Any continuous reactor that allows the introduction of the feedstock, solvent, oxygen-containing gas and catalyst and the separate withdrawal of a vaporous stream and the withdrawal a FDCA-containing product can be used. Such includes the use of a bubble column as suggested in WO 2012/161967. Preferably, the reactor is a continuous stirred tank reactor. This reactor enables a continuous introduction of the starting materials and at the same time allows for an easy withdrawal of the vaporous stream. By means of an overflow, or by an outlet in a side wall or the bottom of the reactor the FDCA-containing product can conveniently be withdrawn. Hence the use of the continuous stirred tank reactor is very advantageous.

The process according to the present invention may be conducted in one reactor. Most preferably, the reaction would be led to completion in one reactor. However, in practice this would require a very long residence time. Therefore, the person skilled in the art would have to accept an incomplete conversion if the residence time is set at a reasonable duration. Typically, the residence time in one reactor is set at such a value that not all starting material has been converted. This may especially be the case in the use of a continuous stirred tank reactor (CSTR) wherein continuously starting material is introduced. Since it is generally desired to convert as much feedstock as possible it is advantageous to conduct the process of the present invention in a plurality of reactors in series. The number of reactors can be selected on the basis of the level of conversion in each of the reactors. Generally, when more than one reactor is used, the number of reactors suitably ranges from two to five. In such a process using more than one reactor, the 5-methoxymethylfurfural-containing feedstock is preferably introduced into the first reactor and at least part of the 2,5-furandicarboxylic acid-containing product that is withdrawn from any reactor is used as feedstock for the subsequent reactor, the 2,5-furandicarboxylic acid-containing product that is withdrawn from the last reactor being recovered. When more than one reactor is used, the reactors are preferably also continuous stirred tank reactors.

In accordance with the present process a vaporous stream containing methyl acetate is withdrawn. The vaporous stream may also comprise different volatile compounds. These compounds include oxygen, that remains after the oxidation reaction, any diluent gases, such as nitrogen, when air, enriched air or lean air is used as oxidizing gas, carbon dioxide, which may be included in the oxidizing gas but which may also be formed during oxidation, methanol that may be formed from 5-methoxymethyl furfural, optionally methyl bromide, that may be formed from the catalyst component, water and acetic acid that may be entrained by the vaporous stream. Since the vaporous stream may comprise a number of components, it is preferred to subject the vaporous stream to one or more treatments to obtain one or more of the components. Preferably, the vaporous stream containing methyl acetate that is withdrawn from the reactor is cooled so that part thereof is condensed to form a condensate, and at least part of the condensate is recycled to the reactor. The cooling of the vaporous stream is preferably conducted in such a way that the condensate formed mainly comprises acetic acid, water and methyl acetate. The condensate may be recycled to the reactor, thereby providing cooling of the reaction mixture in the reactor. It has further surprisingly been found that it is advantageous to recycle only part of the condensate to the reactor. The part of the condensate that is not recycled may vary. Typically, from 10 to 90% wt of the condensate may be recycled. It has been found that if all condensate is recycled, the water in the condensate may lead to a build-up of the water concentration in the reactor which leads to a reduced selectivity and the increase of the methyl acetate concentration in the reactor may lead to further oxidation of methyl acetate and enhanced formation of $CO_2$. The part of the condensate that is not recycled may conveniently be subjected to purification. Especially when acetic acid is comprised in this part of the condensate, it may be economically attractive to recover the acetic acid. Since the condensate may also comprise some methyl acetate, this part of the condensate may preferably be combined with the part of the vaporous stream that is not condensed and subjected to separation, or purification or both. The non-condensed part of the vaporous stream that contains methyl acetate, is preferably, optionally together with a part of the condensate, at least partly subjected to methyl acetate recovery. Suitably all of the non-condensed part of the vaporous stream is subjected to methyl acetate recovery. The recovery of methyl acetate may be carried out in a variety of ways and in a number of stages. Hence, it is feasible to first cool the vaporous stream such that certain gaseous compounds, notably, oxygen, nitrogen and carbon dioxide, are first separated e.g. by flash distillation. In the same or a different stage the heavier compounds, such as methyl acetate, acetic acid, and water are separated, e.g. in a fractionation column. If desired, the compounds separated may be discharged or re-used. The gaseous stream that was first separated, i.e. comprising oxygen, nitrogen, carbon dioxide, may be subjected to a washing treatment, e.g. with water, to remove any environmentally unfriendly compounds that may be comprised in this stream. Subsequently, the gaseous stream may be discharged.

The FDCA-containing product that is withdrawn from the reactor, or in case a plurality of reactors is used, from the last reactor, is being used to recover FDCA, suitably by purification. A suitable manner for such recovery has been disclosed in WO 2012/161967. Such recovery method preferably includes one or more crystallization steps. Subsequently to the crystallization, the solids, comprising FDCA, may be subjected to one or more filtration steps. The filtered solids are suitably subjected to purification that comprises one or more washing steps. The washing step or steps suitably comprise the treatment with one or more washing liquids, selected from water, acetic acid and mixtures thereof. The washing liquids may contain water, acetic acid and FDCA. Therefore, the washing liquid or liquids are subjected to separation of water, and the remainder is at least partly recycled to a reactor. In this way acetic acid may be reused in the oxidation reaction, and the FDCA can be recovered as product in the next cycle.

The reaction conditions in the oxidation reaction of the present invention are mild. The 5-methoxymethylfurfural is suitably allowed to react with oxygen in the presence of acetic acid and the oxidation catalyst at a temperature of 125 to 180° C. and a pressure of 3 to 15 bar. These reaction conditions are especially mild in comparison to those applied in the processes of WO 2010/132740 wherein oxygen partial pressures of 27 to 69 bar are applied. It is clear to the skilled person that the reduced total pressure of 3 to 15 bar will not only be more economical, but will also facilitate the separation of methyl acetate from the reaction mixture in the vapor phase. Since the reaction runs smoothly under these circumstances, the average contact time in the reactor, or in each reactor, as the case may be, suitably ranges from 5 minutes to 2 hours.

BRIEF DESCRIPTION OF THE DRAWING

The FIGURE shows a simplified flow scheme of an embodiment of the process according to the invention wherein two reactors are employed.

DETAILED DESCRIPTION OF THE INVENTION

The FIGURE shows that a feed comprising 5-methoxymethylfurfural is introduced into a reactor, here represented as a continuous stirred tank reactor (CSTR) 5, via a line 1. Into the CSTR 5 also catalyst is introduced via a line 2 and an acetic acid-containing solvent is introduced via a line 3. It is evident that these starting materials may be introduced into the CSTR 5 via separate lines, as indicated herein, but that they may also be combined earlier and be introduced into the CSTR 5 as a combined stream. An oxygen-containing gas, e.g. air, is supplied via a line 4. The gas is compressed to the desired pressure using a compressor 6 and the stream is subsequently split into a partial stream 4a that is introduced into the lower part of the CSTR 5. The reactants are allowed to react in the CSTR 5 to form FDCA and methyl acetate. A vaporous stream containing methyl acetate is withdrawn from the CSTR 5 via a line 7 and passed to a cooling device 8. The cooling device may be any type of cooling device. Suitable apparatuses include indirect heat exchangers. In the cooling device 8 the vaporous stream is partly condensed and the condensate is allowed to leave the cooling device 8 via a line 9. The condensate is the split into a partial stream 10, that is recycled to the CSTR 5 and a remaining stream 11 for further handling. Via a line 20 a gaseous stream is withdrawn from the cooling device 8, which gaseous stream comprises methyl acetate, and the remainder of the oxygen-containing gas. In the case of the use of air, this gaseous stream comprises nitrogen and some oxygen optionally in addition to some methyl acetate and methanol. A 2,5-furandicarboxylic acid-containing product is withdrawn for the CSTR 5 via a line 12. The line 12 may be arranged in the lower part of the CSTR 5, e.g. at the bottom, but it may also be arranged as an overflow of the slurry phase that is being formed in the CSTR 5. Since the stream in line 12 may comprise some unreacted 5-methoxymethyl furfural it is passed to a second reactor, in this case another CSTR 13, where the stream is contacted with an oxygen-containing gas supplied via a line 4b, that is split off from the line 4. Since the stream in line 12 already comprises acetic-acid-containing solvent and catalyst, the required reactants are present in the CSTR 13 and the formation of FDCA may be led to virtual completion. Also from the reaction mixture in the CSTR 13 a vaporous stream is withdrawn, in this case via a line 15. In a cooling device 16, which may be similar to the cooling device 8, the stream in line 15 is partly condensed. The condensate is withdrawn via a line 17, and split into a fraction 18 and a fraction 19. The fraction 18 is recycled to the CSTR 13. To the fraction in line 19 the content of the line 11 is added and the combined contents are passed via the line 19 to a rectification column or stripper 24.

The non-condensed parts of the streams 7 and 15 are withdrawn from the respective cooling devices 8 and 16 via a line 20 and a line 21, respectively. Although the contents of both lines 20 and 21 may be treated separately, the contents of line 21 are suitably added to those of the line 20 and the combined compounds are passed via this line 20 to the rectification column 21. In the rectification column or stripper 24, gases such as nitrogen, oxygen, and volatile compounds, such as methanol are separated from the less volatile compounds, such as methyl acetate, and optionally, acetic acid and water. The gases are withdrawn via a line 23 for disposal (not shown).

From the rectification column or stripper 24 a methyl acetate-containing product is withdrawn via a line 22. If desired, the stream in the line 22 may be subjected to further purification and/or treatment (not shown).

In a way that may be similar to the withdrawal of the stream in the line 12, a product that mainly comprises FDCA is withdrawn from the CSTR 13 via a line 28. The product in the line 28 comprises a slurry of solid FDCA in the acetic-acid-containing solvent. In order to obtain FDCA of a desired purity it may be desirable to subject the product in the line 28 to one or more crystallization and optionally recrystallization steps. The crystallization step has been schematically shown in a crystallization vessel 29 from which a first FDCA product in the form of a slurry is withdrawn via a line 31. The solvent is withdrawn from the vessel 29 via a line 30. The crystallization in the vessel 29 is achieved by cooling and/or depressurizing the FDCA-containing product in the line 28. The FDCA-containing slurry in the line 31 is subjected to further crystallization step in a second crystallization vessel 32, achieved by further cooling and/or depressurizing of the slurry of line 31. The solvent is withdrawn from this vessel via a line 33. The streams in the lines 30 and/or 33 may be separately or combined be recovered and returned to the reaction. This may be accomplished after optional purification or treatment (not shown). A possible treatment is to subject the solvent to a rectification treatment. This may be carried out separately, but it may also be conducted in the rectification column or stripper 24. In such a case, the products of the rectification column or stripper 24 also include acetic acid-containing solvent.

The FDCA that is recovered in the crystallization vessel 32 is withdrawn from the vessel via a line 34. This may conveniently be done in the form of a slurry. To obtain pure FDCA the slurry of the line 34 is suitably passed to a filtration unit 35. In the FIGURE only one filtration unit has been shown. It is evident that several filtration units may be used, if desired. Solid FDCA is filtered from the solvent. Preferably, one or more washing liquids, such as water, acetic acid, or an aqueous solution of acetic acid, is used to purify the FDCA even further. The filtrate, together with the optional washing liquid or liquids, are recovered from the filtration unit 35 via a line 38 and passed to a fractionation column 39. In the fractionation column 39 water and methanol, if present, are separated and discharged via a line 40. Acetic acid in the stream in line 38 is separated from at least part of the water and is withdrawn from the fractionation column 39 via a line 41. The contents of line 41 are advantageously, at least partly, combined with the acetic acid-containing solvent in the line 3, and thus recycled to the reactants in the CSTR 5.

The purified and washed FDCA is recovered as pure FDCA from the filtration unit 35 via a line 37.

It is understood that the FIGURE represents a schematic flow scheme of one embodiment of the process according to the invention. Varieties of such process flow schemes are possible. It is further understood that this schematic flow scheme does not show all auxiliary equipment, such a compressors, heating and cooling devices, pumps etc. The skilled person will understand that these are required where the conditions require such equipment.

The invention will be further illustrated by means of the following Examples

Example 1

A 100 L reactor, equipped with a condenser, was loaded with acetic acid and a catalyst solution. The catalyst solution consisted of water containing 190 g/kg cobalt acetate tetrahydrate, 181 g/kg manganese acetate tetrahydrate and 113 g/kg hydrobromic acid. The amount of acetic acid was 52.8 kg and the amount of catalyst was 3.39 kg. The reactor was heated to 145° C. at a pressure of 18 bar and fed with lean air (8 vol % $O_2$). Subsequently a continuous feed stream of a solution, comprising 15.6 kg methoxymethyl furfural, 0.62 kg of the above catalyst solution and 63.4 kg acetic acid was fed to the reactor at a rate of 35 kg/hr. The reactor was kept at a temperature of 145° C. at a pressure of 14 bar. A vaporous stream was continuously withdrawn from the reactor and passed to the condenser that operated at 20° C. The condensate was collected and analysed. Non-condensed gas was analysed and checked for the presence of $CO_2$.

After two hours the supply of the feed stream to the reactor was stopped and the reactor contents analysed. The selectivity results are shown in the Table below. The total amount of $CO_2$ that was produced per mole of MMF is also shown in the Table.

Comparative Example

In a process wherein no vaporous products are withdrawn, the reactor that was also used in Example 1 was loaded with acetic acid and a catalyst solution. The catalyst solution was the same as in Example 1. The amount of acetic acid was 52.8 kg and the amount of catalyst was 3.50 kg. The reactor was heated to the same temperature and pressure as in Example 1 (viz. 145° C. and 18 bar). Subsequently, a feed stream of a solution, comprising 15.8 kg methoxymethyl furfural, 0.60 kg of the catalyst solution and 8.9 kg acetic acid was fed to the reactor at a rate of 10 kg/h. Lean air (8 vol % oxygen) was fed to the reactor at 50 kg/h. The reactor was kept at a temperature of 145° C. at a pressure of 14 bar for 2 hours. Off gas was analysed for the presence of $CO_2$. Any condensable vapours that escaped from the reaction mixture were condensed and recycled back to the reactor. For comparison reasons the amount of acetic acid was lower than used in Example 1 since in Example 1 acetic acid is consumed by the formation of methyl acetate and also evaporated in the vaporous stream. In this experiment and in Example 1 the methoxymethyl furfural addition rate is the same, viz. about 7 kg/h.

After 2 hours the contents of the reaction mixture was analysed. The selectivity results are shown in the Table below. The total amount of $CO_2$ that was produced per mole of MMF is also shown in the Table.

TABLE

| Example | Selectivity, % mol on solid product | | | Amount $CO_2$, mmol/mol MMF |
| --- | --- | --- | --- | --- |
| | FDCA | FDCAMe | FFCA | |
| Example 1 | 84.2 | 14.1 | 0.7 | 28 |
| Comp. Ex. | 83.8 | 13.3 | 1.4 | 40 |

FDCA = 2,5-furan-dicarboxylic acid;
FDCAMe = mono-methyl ester of FDCA;
FFCA = 5-formyl-furan-2-carboxylic acid.

From the Table it is apparent that a continuous process, as simulated in Example 1, results in less $CO_2$ and thus produces less losses of reactants than a process wherein no organic vapours are withdrawn. Moreover, the solid product appears to contain less by-products. Not only the yield of the mono-methyl ester of FDCA is reduced, but also the production of the incompletely oxidized FFCA is decreased, resulting is a purer FDCA product.

The invention claimed is:

1. A continuous process for the preparation of 2,5-furan-dicarboxylic acid and methyl acetate, comprising:
   introducing a 5-methoxymethyl furfural-containing feedstock, an oxygen-containing gas, an oxidation catalyst and an acetic acid-containing solvent into a reactor;
   allowing 5-methoxymethyl furfural to react with oxygen and acetic acid in the presence of the oxidation catalyst to yield 2,5-furan-dicarboxylic acid as main product and methyl acetate;
   withdrawing 2,5-furan-dicarboxylic acid-containing product from the reactor and recovering 2,5-furan-dicarboxylic acid product; and
   withdrawing a vaporous stream containing methyl acetate from the reactor.

2. The process according to claim 1, wherein the feedstock comprises from 2 to 50% by weight of 5-methoxymethyl furfural, based on the weight of the feedstock, catalyst and solvent.

3. The process according to claim 1, wherein the feedstock, in addition to 5-methoxymethyl furfural, comprises up to 20% by weight 5-hydroxymethyl furfural, based on the weight of the feedstock.

4. The process according to claim 1, wherein the feedstock consists of 50 to 100% by weight of 5-methoxymethyl furfural.

5. The process according to claim 4, wherein the feedstock consists from 90 to 100% by weight of 5-methoxymethyl furfural.

6. The process according to claim 1, wherein the oxygen-containing gas being introduced into the reactor comprises from 6 to 22% by volume oxygen, based on the volume of the oxygen-containing gas.

7. The process according to claim 1, wherein the oxidation catalyst comprises at least one metal selected from the group consisting of cobalt and manganese.

8. The process according to claim 7, wherein the oxidation catalyst comprises cobalt and manganese.

9. The process according to claim 8, wherein the oxidation catalyst comprises both cobalt and manganese in an atomic ratio ranging from 1:1 to 100:1.

10. The process according to claim 8, wherein the catalyst further comprises a source of bromide.

11. The process according to claim 10, wherein the source of bromide is hydrobromic acid.

12. The process according to claim 8, wherein the oxidation catalyst further comprises an additional metal selected from the group consisting of zirconium, cerium, nickel, molybdenum, hafnium, zinc, chromium, ruthenium, iron and mixtures thereof.

13. The process according to claim 1, wherein the concentration of the oxidation catalyst in the reactor is such that it comprises from 500 to 6000 ppm by weight of cobalt and from 20 to 6000 ppm by weight of manganese, based on the weight of the feedstock, solvent and oxidation catalyst.

14. The process according to claim 1, wherein the acetic acid-containing solvent comprises from 1 to 15% by weight water, based on the solvent.

15. The process according to claim 14, wherein the acetic acid-containing solvent comprises from 2 to 6% by weight water, based on the solvent.

16. The process according to claim 1, which is carried out in a plurality of reactors in series.

17. The process according to claim 16, wherein the plurality of reactors comprises reactors that are continuous stirred tank reactors.

18. The process according to claim 16, wherein the average contact time in each reactor of the plurality of reactors ranges from 5 minutes to 2 hours.

19. The process according to claim 16, wherein the number of reactors ranges from two to five.

20. The process according to claim 16, wherein the 5-methoxymethyl furfural-containing feedstock is introduced into the first reactor and at least part of the 2,5-furandicarboxylic acid-containing product that is withdrawn from any reactor is used as feedstock for the subsequent reactor, the 2,5-furan-dicarboxylic acid-containing product that is withdrawn from the last reactor being recovered.

21. The process according to claim 20, wherein the 2,5-furandicarboxylic acid that is withdrawn from the last reactor of a plurality of reactors is subjected to purification.

22. The process according to claim 21, wherein the purification entails one or more crystallization steps.

23. The process according to claim 21, wherein the purification comprises one or more washing steps.

24. The process according to claim 1, wherein the reactor is a continuous stirred tank reactor.

25. The process according to claim 1, wherein the vaporous stream containing methylacetate that is withdrawn from a reactor is cooled so that part thereof is condensed, and part of the condensate is recycled to the reactor.

26. The process according to claim 25, wherein the part of the vaporous stream that is not condensed is at least partly subjected to methyl acetate recovery.

27. The process according to claim 25, wherein the part of the condensate that is not recycled is subjected to methyl acetate recovery.

28. The process according to claim 1, wherein the 2,5-furandicarboxylic acid that is withdrawn from the reactor is subjected to purification.

29. The process according to claim 28, wherein the purification entails one or more crystallization steps.

30. The process according to claim 28, wherein the purification comprises one or more washing steps.

31. The process according to claim 30, wherein the washing steps comprise the treatment with a washing liquid selected from water, acetic acid and mixtures thereof.

32. The process according to claim 31, wherein the washing liquid is subjected to separation of water, the remainder being at least partly recycled to a reactor.

33. The process according to claim 1, wherein the 5-methoxymethyl furfural is allowed to react with oxygen and acetic acid in the presence of the oxidation catalyst at a temperature of 125 to 180° C. and a pressure of 3 to 15 bar.

34. The process according to claim 1, wherein the average contact time in the reactor ranges from 5 minutes to 2 hours.

* * * * *